United States Patent [19]
Winkelmann

[11] Patent Number: 5,563,924
[45] Date of Patent: Oct. 8, 1996

[54] X-RAY APPARATUS HAVING AN ADJUSTABLE PRIMARY RADIATION DIAPHRAGM

[75] Inventor: Helmut Winkelmann, Forchheim, Germany

[73] Assignee: Siemens Aktiengesellschaft, Munich, Germany

[21] Appl. No.: 371,858

[22] Filed: Jan. 12, 1995

[30] Foreign Application Priority Data

Feb. 4, 1994 [DE] Germany ............... 44 03 516.0
Oct. 24, 1994 [DE] Germany ............... 44 37 969.2

[51] Int. Cl.⁶ .................................................. G01N 23/04
[52] U.S. Cl. ...................... 378/150; 378/152; 378/206
[58] Field of Search .......................... 378/145, 146, 378/147, 150, 151, 152, 153, 205, 206, 63

[56] References Cited

U.S. PATENT DOCUMENTS

| | | | |
|---|---|---|---|
| 1,976,179 | 4/1931 | Mannl. | |
| 4,277,684 | 7/1981 | Carson. | |
| 4,672,212 | 6/1987 | Brahme | 378/150 |
| 4,817,125 | 3/1989 | Sklebitz | 378/151 |
| 4,882,741 | 11/1989 | Brown | 378/152 |
| 4,891,833 | 1/1990 | Bernardi | 378/151 |
| 5,136,627 | 8/1992 | Conrads et al. . | |
| 5,299,250 | 3/1994 | Stymol et al. | 378/151 |

FOREIGN PATENT DOCUMENTS

| | | |
|---|---|---|
| 3818542 | 12/1989 | Germany. |
| 3840726 | 6/1990 | Germany. |

OTHER PUBLICATIONS

Patents Abstracts of Japan, P-386 Sep. 7, 1985, vol. 9/No. 221, Application No. 58-190292.

*Primary Examiner*—David P. Porta
*Attorney, Agent, or Firm*—Hill, Steadman & Simpson

[57] ABSTRACT

An x-ray apparatus is provided which allows the diaphragm aperture and the diaphragm position to be precisely identified in a simple manner. For this purpose, a radiation imaging system is provided which produces an image of the aperture of the primary diaphragm on a radiation-electrical transducer, the radiation-electrical transducer on which the aperture is imaged being separate from the radiation detector on which the complete diagnostics image is produced. The radiation-electrical transducer is followed by evaluation electronics for forming electrical signals corresponding to the diaphragm aperture size and position.

2 Claims, 3 Drawing Sheets

X-RAY APPARATUS HAVING AN ADJUSTABLE PRIMARY RADIATION DIAPHRAGM

BACKGROUND OF THE INVENTION

1. Field of the Invention

The present invention is directed to diagnostic x-ray systems which produce a diagnostic x-ray image, and is specifically directed to systems of this type having an adjustable primary radiation diaphragm.

2. Description of the Prior Art

Radiation systems, for example computer tomography systems, are known in the art wherein an x-ray fan beam is generated for diagnostic purposes, the fan beam being formed (gated) by an adjustable primary radiation diaphragm. In known computer tomography systems of this type the primary radiation diaphragm is fashioned as a slit diaphragm, which defines the shape of the x-ray fan beam. The fan beam, in turn, defines the dose profile in the patient, and thus the thickness of the slice in an exposure. The fan beam thus also influences the dose load on the patient and the intensity of the detector signal from which the image data are acquired. For setting various slice thicknesses, it is necessary to set various apertures of the primary radiation diaphragm. In order to achieve an optimally high quantum yield at the radiation detector, it is necessary to insure that the center of area of the radiation fan beam be centrally incident on the detector. This means that the focus of the x-ray radiator, the center line of the primary radiation diaphragm, and the center line of the radiation detector should coincide for an optimum irradiation of the detector. Moreover, in order to insure a low dose load on the patient, it is necessary to minimize the number of required exposures. It is helpful for this purpose if the quality of each individual exposure, and thus its diagnostic content, is optimally high.

In general, the beam geometry is modified by the dynamic influences caused by rotation of the rotating part of the computer tomography apparatus and/or by thermal influences, particularly in the x-ray radiator. Such modification of the beam geometry, if not corrected, can result in a degradation of the image.

SUMMARY OF THE INVENTION

It is an object of the present invention to provide an x-ray apparatus which produces a diagnostic image, and which has an adjustable radiation diaphragm which permits precise deviations of the beam geometry from a desired beam geometry, so that deviations can be corrected when necessary.

The above object is achieved in accordance with the principles of the present invention in an x-ray apparatus having a radiation-electrical transducer on which an image of the primary radiation diaphragm aperture is produced, from which the aperture shape and position can be identified. The radiation-electrical transducer on which the image of the primary radiation diaphragm is produced is a separate element from the radiation detector on which the overall diagnostic image is produced. Output signals from the radiation-electrical transducer are supplied to evaluation electronics, so that the size and position of the primary radiation diaphragm aperture can be identified, and corrective measures can then be undertaken, if either quantity deviates from a desired value.

In the x-ray apparatus disclosed herein, the aperture size and position of the primary radiation diaphragm are identified, preferably relative to the rotating reference plane in the case of computer tomography apparatus. The x-ray apparatus disclosed herein is particularly suited for use with a motor-adjustable primary radiation diaphragm.

DESCRIPTION OF THE PREFERRED EMBODIMENTS

Figure 1:
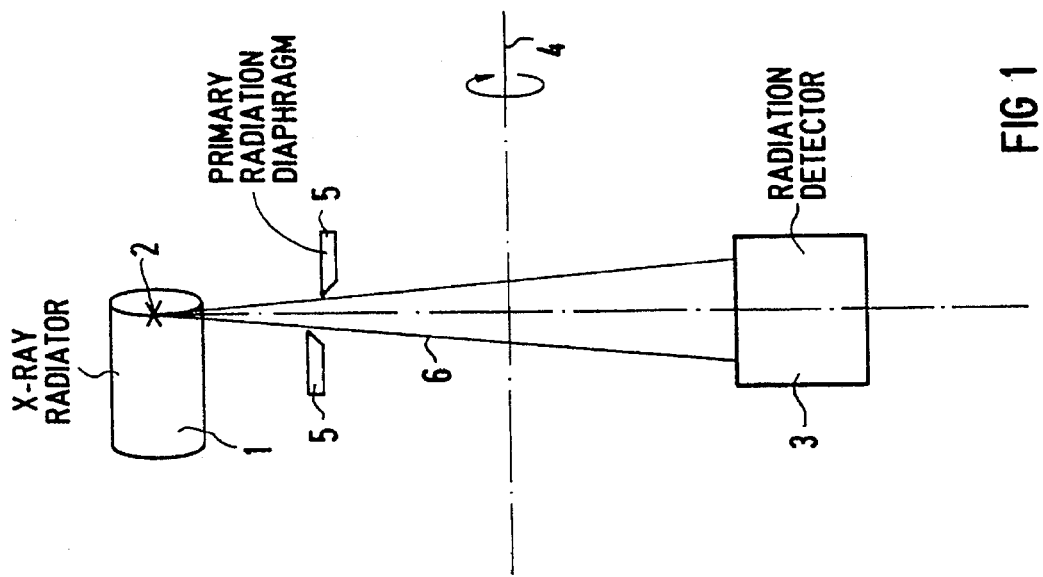
FIG. 1 is a schematic illustration of the basic components of a computer tomography apparatus, for use in explaining the inventive concept.

The rotating part of a computer tomography apparatus is shown in FIG. 1. The apparatus includes an x-ray radiator 1 having a focus 2, and a radiation detector 3. The x-ray radiator 1 and the radiation detector 3 rotate around an axis 4 in a known manner. A primary radiation 5, having an adjustable aperture, generates a fan-shaped x-ray beam 6 which transirradiates a patient (not shown) through which the axis 4 proceeds. The patient is transirradiated from various directions given rotation of the radiation detector 1 and the radiation detector 3, and a computer calculates an image of the transirradiated portion of the patient from the output signals of the radiation detector 3. The fan plane proceeds perpendicularly relative to the plane of the drawing, and the detector 3 is composed of a number of discreet radiation detectors which also extend perpendicularly relative to the plane of the drawing, and are curved around the focus 2. Only those components of the primary radiation diaphragm 5 are shown which define the thickness of the fan-shaped x-ray beam 6. The aperture angle is defined by other parts which are not shown in FIG. 1, and which do not form a part of the invention disclosed herein.

Figure 2:
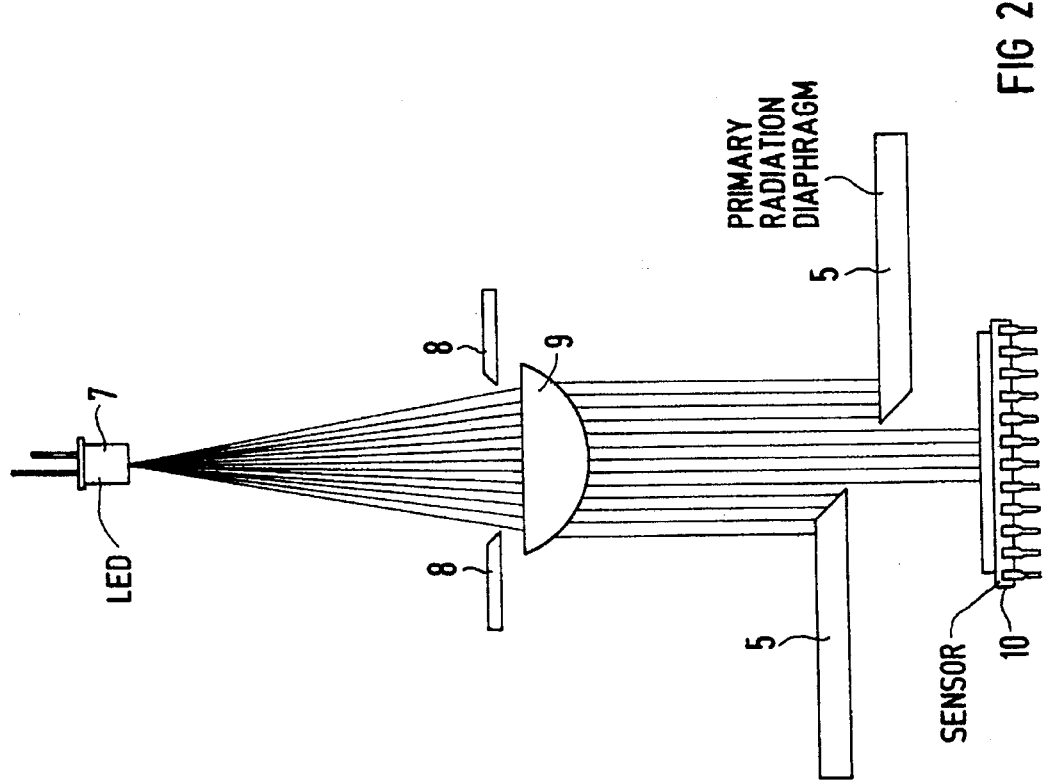
FIG. 2 shows a first optical system for acquiring the size and position of the aperture of the primary radiation diaphragm in the computer tomography apparatus of FIG. 1, in accordance with the principles of the present invention.

An optical system is shown in FIG. 2 for acquiring the diaphragm aperture size and position in the tomography apparatus shown in FIG. 1. The system of FIG. 2 includes a light-emitting diode 7 which emits light through the primary radiation diaphragm 5 via an optical diaphragm 8 and a lens 9. The part of the light which passes through the primary radiation diaphragm 5 is incident on a CCD line sensor 10. The irradiated part of the line sensor 10 thus corresponds to the particular aperture size and position of the primary radiation diaphragm 5. Electrical signals corresponding to the diaphragm aperture size and position are formed from the output signals of the line sensor 10 by suitable evaluation electronics, as described below in combination with FIG. 4. The CCD line sensor 10 is a separate element from the radiation detector 3.

The imaging ensues according to FIG. 2 with a 1:1 imaging scale on the basis of shadow-casting.

It is also possible to employ a more complicated optical system in order to be able to achieve other imaging scales or other functions such as, for example, non-linear imaging, minimization of refraction effects, or minimization of mechanical tolerances.

Figure 3:
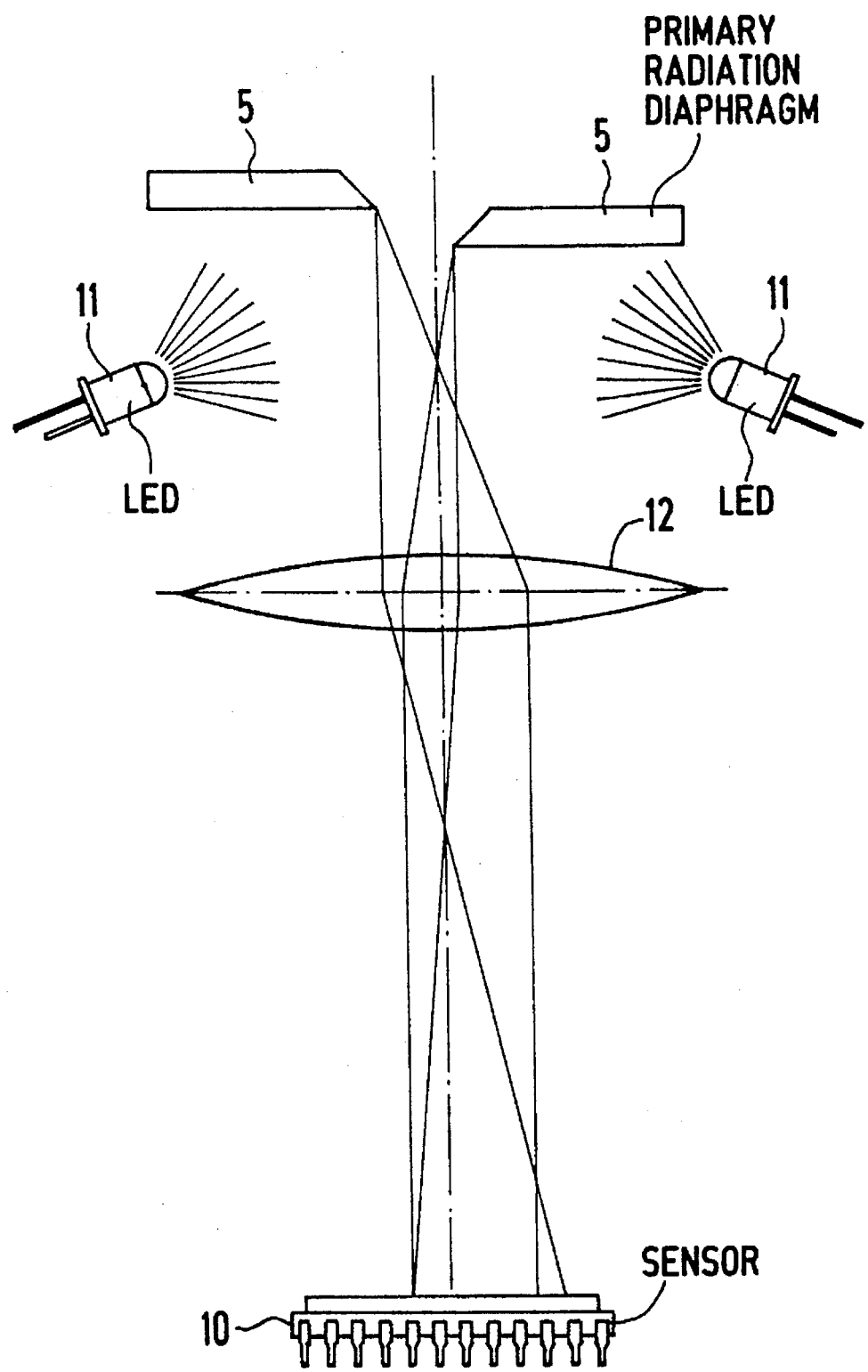
FIG. 3 shows a second optical system for acquiring the size and position of the primary radiation diaphragm aperture in the computer tomography apparatus of FIG. 1, in accordance with the principles of the present invention.

FIG. 3 shows such an optical system wherein two light-emitting diodes 11 shine onto the underside (i.e., the side facing away from the x-ray radiator 1) of the diaphragm plates of the primary radiation diaphragm 5. The plates reflect the light from the light-emitting diodes 11, and the reflected light is directed onto the sensor 10 via a lens 12, and is registered by the sensor 10. Again, the sensor 10 is a separate element from the radiation detector 3.

Instead of a separate light source for illuminating the sensor 10, it is also possible to exploit the x-ray radiation which is already being generated. A regulation of the illumination level is useful in order to compensate for aging effects and contamination effects and in order to optimally modulate the sensor 10, as well as to be able to recognize outage of the illumination unit, if it occurs. To this end, the intensity of the light-emitting diodes 7 and 11 can be made variable in the embodiments shown in FIGS. 2 and 3. Moreover, other sensors, for example a photodiode array, may be employed as the sensor 10 instead of a CCD line sensor. Given the illustrated CCD line sensor 10, a locational identification of the edges of the primary radiation diaphragm 5 can be made simply by counting the illuminated pixels, given a predetermined pixel spacing.

Other sensors such as, for example, PSD (position sensitive device) sensors can be employed, wherein measurement of the diaphragm position ensues indirectly via an intensity measurement on the basis of the center of gravity formation, in a manner which is known in the art, and by measuring the size of the aperture image thereon.

Figure 4:
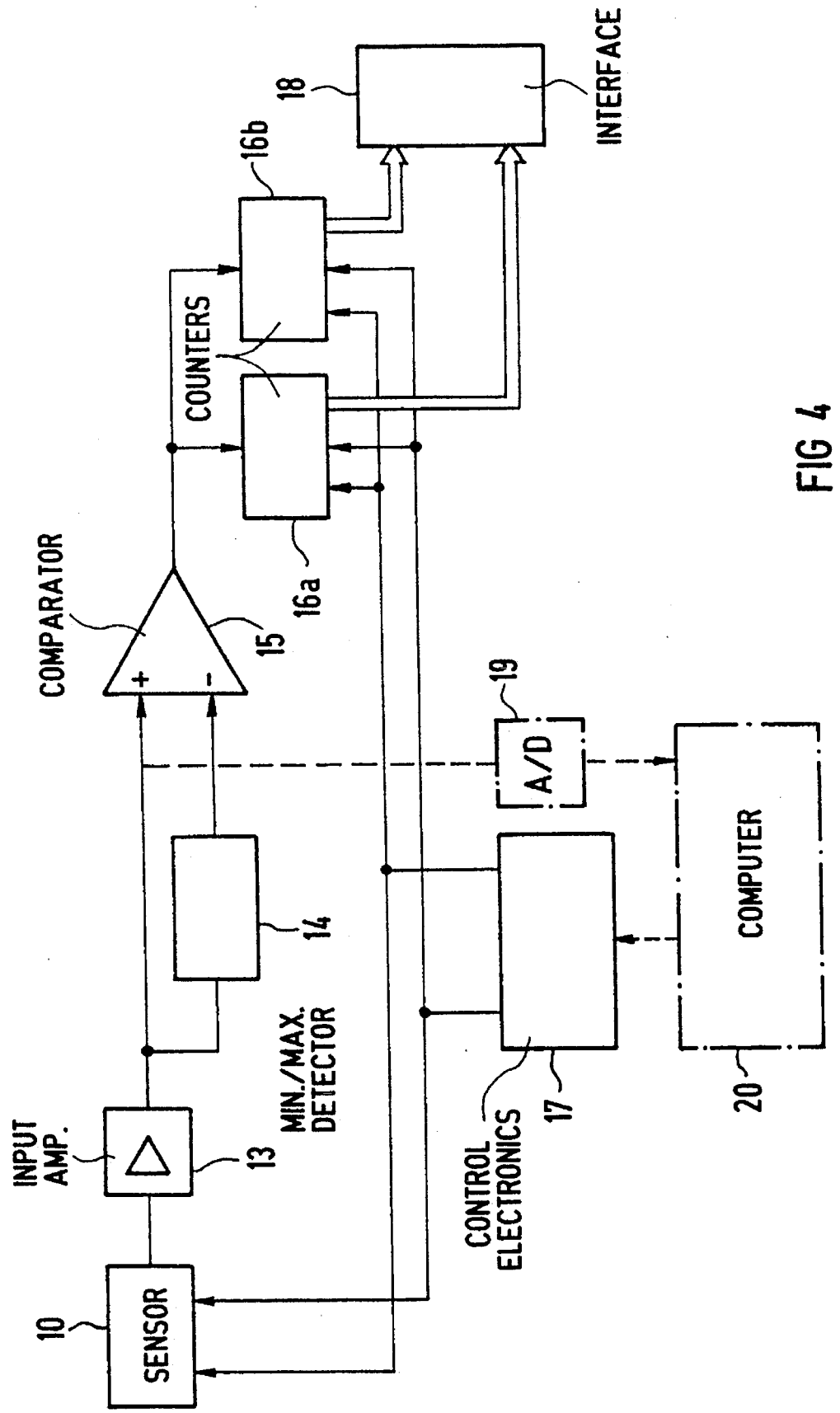
FIG. 4 is a block diagram of evaluation electronics for evaluating the signals obtained from either of the optical systems shown in FIGS. 2 and 3, in accordance with the principles of the present invention.

As shown in FIG. 4, the sensor 10 is connected to an input amplifier 13 of evaluation electronics. The amplifier 10 is for offset and level matching of the CCD output signal, plus filtering as needed, for conditioning the signal which is supplied to the remainder of the evaluation electronics. The output signal from the input amplifier 13 is supplied to a Min/Max. detector 14 which identifies the minimum and maximum brightness for the determination of a comparison threshold. The output of the min/max detector 14 is supplied to one input of a comparator 15, to which the output from the input amplifier 13 is also supplied. The comparator 15 identifies the bright and dark pixels of the sensor 10. The output of the comparator 15 is supplied to two counters 16a and 16b for determining the chronological references, and thus the spatial reference of the bright/dark transitions. One counter counts the time (i.e., the number of pixels) until the first dark/bright transition is reached, and the other counter counts the time (i.e., the number of pixels) until the first bright/dark transition is reached.

Control electronics 17 generate the various signals necessary for sequencing the evaluation procedure. The control electronics 17 generates, for example, the start signal for starting the read-out of a new line of the sensor 10, signals for resetting the counters 16a and 16b, and a clock signal for controlling read-out of a line of the sensor 10 and for incrementing the counters 16a and 16b.

The outputs of the counters 16a and 16b are supplied to an interface 18 to a higher-ranking system, for example a computer or a display unit (not shown).

Optionally, an analog-to-digital converter 19 can be provided for acquiring each pixel individually in combination with a computer 20.

The evaluation is based on the fact that, by the operation of the sensor 10, there is a strict relationship between the time axis of the output signal and the position axis of the sensor 10, so that conclusions regarding the location of the aperture imaged thereon can be made by making a time identification. Since the imaging of the edges of the aperture usually does not ensue sharply enough so that a bright-dark transition will occur precisely between one pixel and its neighboring pixels (the transition usually being distributed over a number of pixels), a decision or a comparison threshold is undertaken which defines the location (time) at which a transition from bright to dark or from dark to light is made. For example, the threshold can be identified as an average value of the bright and dark pixels, and may also serve the purpose of brightness control of the illumination unit.

The simultaneous measurement of the diaphragm aperture size and position has the following consequences:

The demands made on the stability of the focus location of the x-ray radiator 1 (thermal focus motion and position of the installation location) can be reduced, because the primary radiation diaphragm 5 can be re-adjusted given a movement of the focus location. Moreover, dynamic influences (for example, gravitation and centrifugal force) can be corrected by re-adjusting the primary radiation diaphragm 5 during the image pickup. The effective aperture of the primary radiation diaphragm 5 (and thus, the slice thickness) can easily be identified. The adjustment can be simplified because manual mechanical adjustment in conjunction with the motor-adjustment of the primary radiation diaphragm 5 is not necessary, and an absolute scale for the diaphragm motion is established by the position of the sensor 10. Moreover, if separate sensors are disposed to the left and right of the primary radiation diaphragm 5, tilting of the primary radiation diaphragm 5 can be recognized and can be reported at the same time as the aperture size and position are being reported and, depending on the details of the diaphragm adjustment mechanism, such tilting may be simultaneously compensated.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray apparatus for examining a subject, comprising: an x-ray source which emits x-rays;

a primary radiation diaphragm having an adjustable diaphragm aperture disposed following said x-ray source in a direction of propagation of said x-rays, said primary radiation diaphragm gating said x-rays to form an x-ray beam;

radiation detector means, disposed following said primary radiation diaphragm in said propagation direction, for detecting x-rays in said x-ray beam attenuated by a subject and for generating signals comprising a diagnostic image of said subject;

means for producing an image of said aperture comprising a light source disposed at a side of said primary radiation diaphragm facing said x-ray source and emitting light which passes through said aperture;

radiation-electrical transducer means, separate from said radiation detector means, on which said image of said aperture is incident, for generating electrical signals identifying a size and position of said aperture; and evaluation means, supplied with said electrical signals from said radiation-electrical transducer means, for identifying said position and size of said aperture.

2. An x-ray apparatus as claimed in claim 1 further comprising means on which said x-ray source and said radiation detector means are mounted for rotating said x-ray source and said radiation detector means around an axis.

* * * * *